United States Patent
Taguchi et al.

(10) Patent No.: US 7,807,859 B2
(45) Date of Patent: Oct. 5, 2010

(54) POLYMERIZATION INHIBITOR FOR TETRAFLUOROETHYLENE

(75) Inventors: Mai Taguchi, Osaka (JP); Kenji Otoi, Osaka (JP); Yoshiyuki Takase, Osaka (JP); Hideya Saitou, Osaka (JP); Yoshiyuki Hiraga, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 92 days.

(21) Appl. No.: 12/120,796

(22) Filed: May 15, 2008

(65) Prior Publication Data

US 2008/0287715 A1    Nov. 20, 2008

(30) Foreign Application Priority Data

May 15, 2007    (JP)  .......................... P2007-129135
Nov. 21, 2007    (JP)  .......................... P2007-301870

(51) Int. Cl.
    *C07C 17/38*     (2006.01)
(52) U.S. Cl. .................................................... 570/178
(58) Field of Classification Search ................. 570/178
    See application file for complete search history.

(56) References Cited

U.S. PATENT DOCUMENTS

| 2,737,533 | A | 3/1956 | Marks et al. |
| 3,834,996 | A | 9/1974 | Aiso et al. |

FOREIGN PATENT DOCUMENTS

| EP | 0724148 A1 | 7/1996 |
| GB | 1317517 | 5/1973 |

*Primary Examiner*—Jafar Parsa
(74) *Attorney, Agent, or Firm*—Sughrue Mion, PLLC

(57) ABSTRACT

The present invention provides a polymerization inhibitor preventing the self-polymerization of TFE and the generation of a modified polymer of a polymerization inhibitor in a distillation step, particularly in a rectification step, of TFE. The present invention provides a method of distilling tetrafluoroethylene in the presence of a polymerization inhibitor comprising a cyclohexadiene compound of the formula:

$$R^1\text{-}A\text{-}R^2$$

wherein $R^1$ is a hydrocarbon group having 1 to 5 carbon atoms, $R^2$ is a hydrogen atom or a hydrocarbon group having 1 to 5 carbon atoms, and A is a cyclohexadiene ring. The cyclohexadiene compound is preferably α-terpinene or γ-terpinene.

2 Claims, No Drawings

POLYMERIZATION INHIBITOR FOR TETRAFLUOROETHYLENE

FIELD OF THE INVENTION

The present invention relates to a method of preventing the clogging caused by self-polymerization of tetrafluoroethylene and by a modified polymer of a polymerization inhibitor in a distillation step, particularly in a rectification step, of tetrafluoroethylene.

BACKGROUND ART

Generally, tetrafluoroethylene (referred to as "TFE") having high purity has extremely high polymerizability. It is remarkable, when particularly a very small amount of oxygen is contained. It is known to sometimes polymerize explosively.

Thus, when TFE is stored, a polymerization inhibitor, for example, a terpenoid is added in the amount of around 100-10000 ppm (U.S. Pat. No. 2,737,533). There is disclosed a rectification method comprising adding a terpene mixture containing α-pinene, camphene, α-terpinene, D-limonene, γ-terpinene, p-cymene and/or terpinolene so as to prevent the self-polymerization of TFE in a rectifying column simultaneously with lowing the oxygen concentration by absorbing oxygen in TFE, when TFE is rectified (U.S. Pat. No. 3,834,996).

However, the effect of preventing the polymerization of this terpene mixture is not enough in a top of the rectifying column. Polytetrafluoroethylene (hereinafter referred to as "PTFE") generated by the self-polymerization of TFE accumulates on a tray of the column top, the tray is clogged up with this PTFE so that the operation trouble of the rectifying column is caused. Further, it has been found that the terpene mixture reacts with oxygen and/or acid to give a viscous oligomer compound. When such viscous material has accumulated on the tray of the rectifier, the flooding is caused by a differential pressure increase as by PTFE accumulating. When the flooding occurs, the quality is affected because of poor separation and the throughput should be reduced to have a fear of an influence on productivity.

Disclosed is a method to add α-methyl vinyl benzene and α-methyl vinyl methylbenzene as the inhibitor giving no modified viscous material (U.S. Pat. No. 2,737,533). However, the prevention of polymerization of TFE is said to be effective in a storage step and a transportation step, but enough performance of preventing polymerization can not be obtained in the rectification step.

[Patent document 1] U.S. Pat. No. 2,737,533
[Patent document 2] U.S. Pat. No. 3,834,996

DISCLOSURE OF THE INVENTION

Problems to be Solved by the Invention

From the above-mentioned points of view, a polymerization inhibitor preventing the self-polymerization of TFE in a distillation step (particularly, a rectification step) of TFE, which is not modified to give a polymer, is strongly required.

Means for Solving the Problems

In a rectification step of TFE, the use of, as a polymerization inhibitor, a cyclohexadiene compound satisfying both of oxygen elimination and polymerization prevention and giving no modified polymer prevents the clogging caused by PTFE and the clogging caused by viscous terpene.

The gist of the present invention resides in a method of distilling tetrafluoroethylene in the presence of a polymerization inhibitor comprising a cyclohexadiene compound of the formula:

wherein $R^1$ is a hydrocarbon group having 1 to 5 carbon atoms,
$R^2$ is a hydrogen atom or a hydrocarbon group having 1 to 5 carbon atoms, and
A is a cyclohexadiene ring.

Effect of the Invention

According to the present invention, TFE can be stably rectified, since the clogging caused by PTFE in the rectification step of TEE and the clogging caused by the modified product of the polymerization inhibitor can be prevented.

BEST MODE FOR CARRYING OUT THE INVENTION

The present invention uses, as the polymerization inhibitor, the cyclohexadiene compound of the formula:

wherein $R^1$ is a hydrocarbon group having 1 to 5 carbon atoms,
$R^2$ is a hydrogen atom or a hydrocarbon group having 1 to 5 carbon atoms, and
A is a cyclohexadiene ring.
In a formula (I), $R^1$ and $R^2$ may be bonded to any position of A (the cyclohexadiene ring).
Examples of the cyclohexadiene compound are as follows:

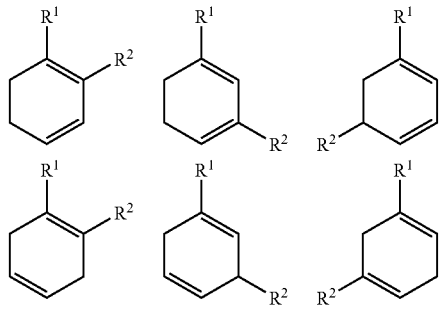

Generally, $R^1$ and $R^2$ are an alkyl group having 1 to 5 carbon atoms.
$R^1$-A-$R^2$ is preferably

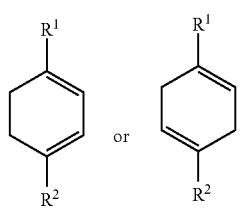

wherein $R^1$ and $R^2$ are the same as defined above.

Specific examples of $R^1$ and $R^2$ are a methyl group, an ethyl group, a propyl group, a butyl group and a pentyl group. Preferably, $R^1$ is a methyl group, an ethyl group, a propyl group, a butyl group or a pentyl group, and $R^2$ is a propyl group, a butyl group or a pentyl group. At least one of $R^1$ and $R^2$ preferably has a tertiary carbon atom. Preferably, the propyl group is an isopropyl group, the butyl group is an isobutyl group, and the pentyl group is an isopentyl group.

Particularly preferably, the cyclohexadiene compound is α-terpinene, that is,

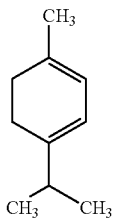

or γ-terpinene, that is,

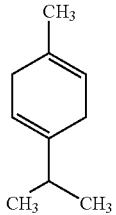

The cyclohexadiene compound preferably has such vapor pressure as a polymerization prevention effect is exhibited even in the top of rectifying column having high oxygen concentration. The vapor pressure of the cyclohexadiene compound is preferably at least 100 Pa, for example, from 100 to 600 Pa at 25 degrees Celsius. The cyclohexadiene compound easily reacts with oxygen and is not modified by an oxidation reaction to give a strongly viscous liquid.

The amount of the cyclohexadiene compound is preferably from 0.1 to 400 micro-mol, particularly from 0.1 to 50 micromol, based on 1 mol of TFE in a gas phase. The cyclohexadiene compound is a single compound or a mixture of plural compounds.

The distillation may be in any step of distilling TFE, but is preferably rectification. In the distillation, the pressure may be, for example, from 0.34 to 3.7 MPa, and the temperature may be from −50 to 30 degrees Celsius. More preferably, the pressure is from 1.2 to 2.0 MPa, and the temperature is from −15 to 5 degrees Celsius.

By the distillation, TFE becomes a vapor phase from a liquid phase and subsequently becomes a liquid to make TFE purer.

A quantity measurement method of the TFE self-polymerization prevention effect of the present invention comprises absorbing a TFE gas containing the predetermined concentration of the inhibitor into silica gel, and measuring the weight increase of the silica gel. The increase amount of the silica gel is the adhesion amount of polytetrafluoroethylene (PTFE) produced by the polymerization of TFE at the surface of the silica gel caused by heat of adsorption evolved by adsorption of TFE to silica gel.

EXAMPLE

The present invention is explained specifically by the following Examples, but the present invention is not limited to these Examples.

Test Example 1

Each of α-pinene, α-terpinene, 1,4-cineol, D-limonene, 1,8-cineol, γ-terpinene, p-cymene and terpinolene (products manufactured by Japan Terpene Company) in amount of 20 $cm^3$ was charged into a glass vial of 50 $cm^3$, and the vial was left in a draft. After the oxidation under left state for one month, a specific gravity change is measured, and analysis by gas. chromatograph (GC) and nuclear magnetic resonance (NMR) was performed. The experiment results are shown in table 1.

TABLE 1

| Inhibitor | Change amount of specific gravity | GC composition change | NMR | Viscosity change |
| --- | --- | --- | --- | --- |
| α-Pinene | 0.00 | None | No change | No change |
| α-Terpinene | 0.11 | Appearance of peak of high boiling point material | p-Cymene generation | No change |
| 1,4-Cineol | 0.04 | None | No change | No change |
| D-Limonene | 0.04 | Appearance of peak of high boiling point material | Oligomer generation | Increase |
| 1,8-Cineol | 0.00 | None | No change | No change |
| γ-Terpinene | 0.02 | Increase of low point material | p-Cymene generation | No change |
| p-Cymene | 0.00 | None | No change | No change |
| Terpinolene | 0.14 | Increase of high and low point materials | Aromatic compound generation | Remarkable increase |

α-Pinene, cineol and the p-cymene are inconvenient, since they do not react with oxygen, that is, do not remove oxygen.

It is α-terpinene and terpinolene that has a remarkably high specific gravity change by the air oxidation. γ-Terpinene has a small specific gravity change, but the composition greatly varies. α-Terpinene, terpinolene and γ-terpinene easily react with oxygen. From the results of NMR measurement, it is understood that p-cymene generates after the oxidation of α-terpinene and γ-terpinene.

On the other hand, The D-limonene generates an oligomer by oxidation reaction. Terpinolene is inconvenient, since a composition change is the largest, and the aromatic compound different from p-cymene generates after the oxidation reaction and has the remarkably increased viscosity.

Comparative Example 1

Three 6.9 $cm^3$ pressure-resistant containers containing 3.81 g, 3.66 g and 3.71 g, respectively, of silica gel (HISHI BEAD N, manufactured by DOKAI CHEMICAL INDUSTRIES CO LTD.) heat-treated at 150 degrees Celsius for 20 hours were depressurized, and oxygen was removed till oxygen concentration became 1.4 ppm. Consequently, a mixture gas (TFE/$N_2$=73.2/26.8) of TFE and nitrogen free of inhibitor was charged at room temperature till 0.51 MPa of an internal pressure of the container. The container was opened 24 hours later, and the weight increase of the silica gel was measured. Results are shown in Table 2. The used silica gel had a color changed to white.

Example 1

Three 6.9 cm³ pressure-resistant containers containing 3.88 g, 3.78 g and 3.85 g, respectively, of silica gel (HISHI BEAD N, manufactured by DOKAI CHEMICAL INDUSTRIES CO LTD.) heat-treated at 150 degrees Celsius for 20 hours were depressurized, and oxygen was removed till oxygen concentration became 0.8 ppm. Consequently, a mixture gas (TFE/N₂=73.2/26.8) of TFE and nitrogen containing 5.84 mol ppm, 9.02 mol ppm and 14.91 mol ppm of α-terpinene (a product manufactured by TOKYO CHEMICAL INDUSTRIES CO. LTD.) was charged at room temperature till 0.51 MPa of an internal pressure of the container. The container was opened 24 hours later, and the weight increase of the silica gel was measured.

Results are shown in Table 2.

Comparative Example 2

Three 6.9 cm³ pressure-resistant containers containing 3.67 g, 3.77 g and 3.76 g, respectively, of silica gel (HISHI BEAD N, manufactured by DOKAI CHEMICAL INDUSTRIES CO LTD.) heat-treated at 150 degrees Celsius for 20 hours were depressurized, and oxygen was removed till oxygen concentration became 1.8 ppm. Consequently, a mixture gas (TFE/N₂=73.2/26.8) of TFE and nitrogen containing 5.79 mol ppm, 8.16 mol ppm and 11.10 mol ppm of α-pinene (a product manufactured by TOKYO CHEMICAL INDUSTRIES CO. LTD.) was charged at room temperature till 0.51 MPa of an internal pressure of the container. The container was opened 24 hours later, and the weight increase of the silica gel was measured. Results are shown in Table 2.

Comparative Example 3

Three 6.9 cm³ pressure-resistant containers containing 3.81 g, 3.72 g and 3.74 g, respectively, of silica gel (HISHI BEAD N, manufactured by DOKAI CHEMICAL INDUSTRIES CO LTD.) heat-treated at 150 degrees Celsius for 20 hours were depressurized, and oxygen was removed till oxygen concentration became 1.8 ppm. Consequently, a mixture gas (TFE/N₂=73.2/26.8) of TFE and nitrogen containing 5.40 mol ppm, 7.01 mol ppm and 17.24 mol ppm of D-limonene (a product manufactured by TOKYO CHEMICAL INDUSTRIES CO. LTD.) was charged at room temperature till 0.51 MPa of an internal pressure of the container. The container was opened 24 hours later, and the weight increase of the silica gel was measured. Results are shown in Table 2.

TABLE 2

|  | Inhibitor | | Increase |
| --- | --- | --- | --- |
|  | Type | Concentration (mol ppm) | amount (g/g-silica gel) |
| Comparative Example 1 | — | — | 0.039 |
|  | — | — | 0.046 |
|  | — | — | 0.043 |
| Example 1 | α-Terpinene | 5.84 | 0.023 |
|  | α-Terpinene | 9.02 | 0.016 |
|  | α-Terpinene | 14.91 | 0.005 |
| Comparative Example 2 | α-Pinene | 5.79 | 0.030 |
|  | α-Pinene | 8.16 | 0.013 |
|  | α-Pinene | 11.10 | 0.011 |
| Comparative Example 3 | D-Limonene | 5.4 | 0.016 |
|  | D-Limonene | 7.01 | 0.005 |
|  | D-Limonene | 17.24 | 0.008 |

It is understood from table 2 that α-terpinene prevents the self-polymerization of TFE under the condition of low oxygen concentration of at most 1.8 mol ppm, better compared to α-pinene and D-limonene.

The invention claimed is:

1. A method of distilling tetrafluoroethylene in the presence of a polymerization inhibitor comprising a terpene, wherein more than 90 wt % of the terpene is α-terpinene represented by the formula:

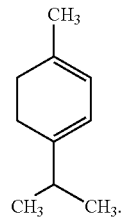

2. A method as claimed in claim 1, wherein the clogging caused by the self-polymerization of polytetrafluoroethylene and the clogging caused by the polymerization inhibitor are prevented.

* * * * *